(12) United States Patent
Fitchett et al.

(10) Patent No.: US 9,139,681 B2
(45) Date of Patent: Sep. 22, 2015

(54) METHOD OF FORMING A RESIN FROM AN ALDEHYDE OIL

(75) Inventors: Colin Fitchett, Duxford (GB); Colin Chappell, Duxford (GB)

(73) Assignee: CAMBRIDGE BIOPOLYMERS LIMITED, Cambridgeshire (GB)

( * ) Notice: Subject to any disclaimer, the term of this patent is extended or adjusted under 35 U.S.C. 154(b) by 319 days.

(21) Appl. No.: 13/514,781

(22) PCT Filed: Dec. 10, 2010

(86) PCT No.: PCT/GB2010/002257
§ 371 (c)(1),
(2), (4) Date: Sep. 27, 2012

(87) PCT Pub. No.: WO2011/070332
PCT Pub. Date: Jun. 16, 2011

(65) Prior Publication Data
US 2013/0116386 A1 May 9, 2013

(30) Foreign Application Priority Data
Dec. 10, 2009 (GB) .................................. 0921666.4

(51) Int. Cl.
- C08G 6/00 (2006.01)
- C08G 8/28 (2006.01)
- C08G 8/00 (2006.01)
- C07C 47/00 (2006.01)
- C08G 4/00 (2006.01)
- C08G 8/26 (2006.01)
- C08G 8/32 (2006.01)
- C08G 8/04 (2006.01)

(52) U.S. Cl.
CPC . *C08G 8/28* (2013.01); *C07C 47/00* (2013.01); *C08G 4/00* (2013.01); *C08G 6/00* (2013.01); *C08G 8/00* (2013.01); *C08G 8/04* (2013.01); *C08G 8/26* (2013.01); *C08G 8/32* (2013.01)

(58) Field of Classification Search
None
See application file for complete search history.

(56) References Cited

U.S. PATENT DOCUMENTS 3,112,329 A * 11/1963 Pryde et al. ............... 554/120
4,588,613 A    5/1986 Liau et al.
(Continued)

FOREIGN PATENT DOCUMENTS

| CN | 1803874 | * 11/2005 |
|----|---------|-----------|
| GB | 950623 A | 10/1960 |

(Continued)

OTHER PUBLICATIONS

Rossouw, Journal of Polymer Science: Polymer Chemistry Edition, vol. 18, Issue 12, Mar. 2003.*

(Continued)

*Primary Examiner* — Robert C Boyle
(74) *Attorney, Agent, or Firm* — Scully, Scott, Murphy & Presser, P.C.

(57) ABSTRACT

The present invention relates to methods for the production of a resin such as a thermosetting resin, particularly a bioresin, components for use in the methods, and products obtained from the methods. In one aspect the method of forming a resin comprising the steps of: (1) providing an aldehyde-cross-linking agent condensate obtained by reacting a volatile aldehyde with a cross-linking agent; (2) providing a non-volatile aldehyde; and (3) combining the aldehyde-cross-linking agent condensate and the non-volatile aldehyde, thereby forming the resin.

33 Claims, 3 Drawing Sheets

(56) References Cited

U.S. PATENT DOCUMENTS

| | | | |
|---|---|---|---|
| 6,768,029 B1 * | 7/2004 | Khan et al. | 568/469 |
| 7,538,236 B2 * | 5/2009 | Narine et al. | 554/133 |
| 2002/0004576 A1 * | 1/2002 | Khan et al. | 528/2 |
| 2004/0242828 A1 | 12/2004 | Khan et al. | |
| 2005/0010069 A1 | 1/2005 | Fitchett et al. | |
| 2007/0175793 A1 | 8/2007 | Narine et al. | |

FOREIGN PATENT DOCUMENTS

| | | |
|---|---|---|
| GB | 2 392 163 A | 2/2004 |
| WO | WO 00/78699 A1 | 12/2000 |
| WO | WO 03/050081 A1 | 6/2003 |
| WO | WO 2008/073729 A2 | 6/2008 |

OTHER PUBLICATIONS

Pryde, Journal of the American Oil Chemists' Society, Jul. 1961, vol. 38, Issue 7, pp. 375-379.*

Computer Translation of CN 1803874—Nov. 2005.*

Guo A. et al., "Polyols and Polyurethanes from Hydroformylation of Soybean Oil", Journal of Polymers and the Environment 10(112):49-52 (Apr. 2002).

Kandanarachchi P. et al., "Kinetics of the Hydroformylation of Soybean Oil by Ligand-Modified Homogeneous Rhodium Catalysis", JAOCS 79(12):1221-1225 (Dec. 2002).

International Search Report and Written Opinion dated May 16, 2011 received from the European Patent Office from Application No. PCT/GB2010/002257.

UK Search Report dated Aug. 17, 2010 received from Application No. GB0921666.4.

* cited by examiner

METHOD OF FORMING A RESIN FROM AN ALDEHYDE OIL

The present invention relates to methods for the production of a resin such as a thermosetting resin, particularly a bioresin, components for use in the methods, and products obtained from the methods.

Resins such as thermosetting resins are widely used in industry for example in timber board composites, insulation, foundry castings, automotive applications, laminates, coatings, and agricultural fibre composites. Resins may be used for example for their properties as adhesives or for their ability to serve as a matrix filler in composites made from fibres, particles, etc. Resins may be formed by combining an aldehyde with a cross-linking agent (also known in the art as a "cross-linker") such as phenolic compounds (including resorcinol, i.e. 1,3-dihydroxy benzene; CAS 108-46-3), urea (CAS 57-13-6), amines or polyols.

In turn, aldehydes may be derived from the oxidative cleavage of an unsaturated bond in plant or animal oils. Oxidative cleavage may be effected by ozone, followed by the catalytic reduction of the oxidised intermediates to form a mixture of reactive aldehydes (also known as "aldehyde oil"), for example as disclosed in Pryde et al. (1961, J. Am. Oil Chem. Soc. 38: 375-379), WO00/78699 and WO03/050081.

Aldehydes for use in resin formation may also be derived using hydroformylation, in which a formyl group (CHO) and a hydrogen atom are added across a carbon-carbon double bond present in unsaturated fatty acids using a catalyst such as rhodium or cobalt. The use of hydroformylation to form aldehydes from vegetable oils, for example soybean oil, has been described in Guo et al. (2002, J. Polymers Environ. 10: 49-52), Kandanarachchi et al. (2002, J. Mol. Catal. A: Chem. 184: 65-71) and WO2008/073729.

Figure 1:
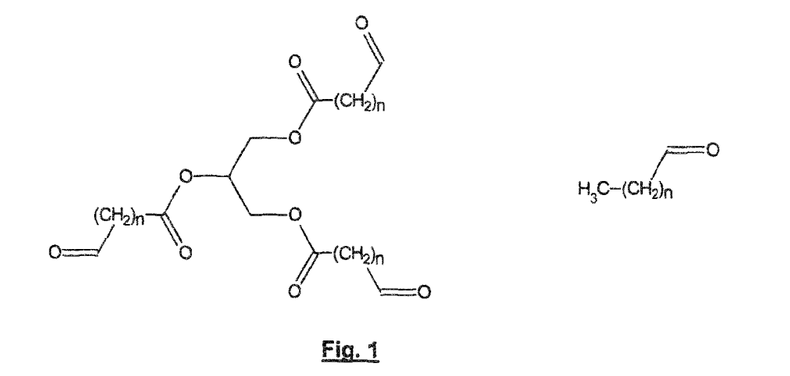
FIG. 1 shows the chemical structures of glyceride-bound aldehyde and nonanal as generated from the reductive ozonolysis of an idealised triolein vegetable oil (prior art)

If an aldehyde oil is produced by reductive ozonolysis from an "idealised" vegetable oil in the form of pure glyceryl ester of oleic acid (i.e. triolein), the products would be primarily glyceride-bound aldehyde ($C_{30}H_{50}O_9$) and nonanal ($C_9H_{18}O$), as shown in FIG. 1. However, suitable vegetable oils are usually a mixture of at least glyceryl esters of monounsaturated oleic acid, polyunsaturated linoleic and linolenic acids, with some saturated acids such as stearic and palmitic acids. This means that upon reductive ozonolysis, the products are more diverse but comprise mainly glyceride-bound aldehydes (for example but not limited to $C_{30}H_{50}O_9$) plus $C_9H_{18}O$ (nonanal), $C_6H_{12}O$ (hexanal), $C_3H_6O$ (propanal). The higher the content of oleic acid the more nonanal is produced, the higher the linoleic acid the more hexanal is produced, and the higher the linolenic acid the more propanal is produced. In a typical rapeseed oil-derived product of reductive ozonolysis, for example, there will be around 70-75% glyceride-bound aldehydes, 16-22% nonanal, 1-3% hexanal and traces of propanal, heptanal and malonaldehyde (as called malondialdehyde).

Figure 2:
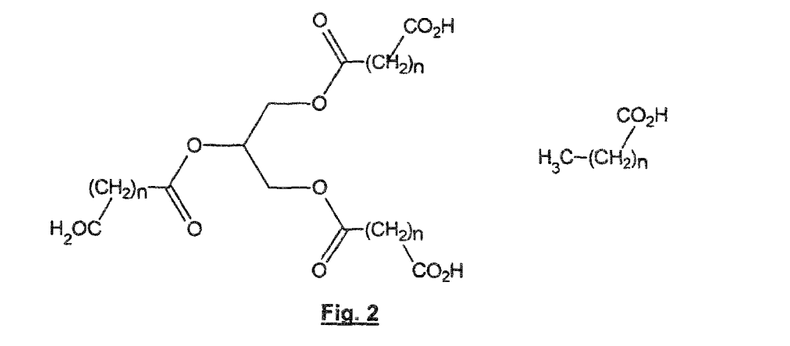
FIG. 2 shows the minority products glyceride-bound acid and nonanoic acid as generated from the reductive ozonolysis of an idealised triolein vegetable oil (prior art)

Also, as a consequence of the reductive ozonolysis process, in addition to aldehydes traces of acids are produced. In the triolein example mentioned above, these acids would be $C_{30}H_{50}O_{12}$ (glyceride-bound acids) and $C_9H_{18}O_2$ (nonanoic acid), as depicted in FIG. 2. In a more typical case there will, in addition, be traces of hexanoic acid, propanoic acid and formic acid.

Prior art methods for formation of resins from aldehyde oils have typically involved combining the aldehyde oil products with a cross-linking agent such as a nucleophile. In some methods, any volatile aldehydes such as nonanal, hexanal and propanal in the aldehyde oils were considered to be less useful for cross-linking to form resins, and therefore removed. The remaining non-volatile aldehydes such as the glyceride-bound acids were then reacted with a cross-linking agent to yield cross-linked polymer resins (see Pryde et al., 1961, supra).

The present invention provides alternative methods of producing a resin such as a thermosetting bioresin, as well as components for use in, and products obtained from, these methods.

According to a first aspect of the present invention, there is provided a method of forming a resin, comprising the steps of:

(1) providing an aldehyde-cross-linking agent condensate obtained by reacting a volatile aldehyde, for example from an aldehyde oil, with a cross-linking agent;

(2) providing a non-volatile aldehyde, for example a glyceride-bound aldehyde such as from an aldehyde oil; and (3) combining the aldehyde-cross-linking agent condensate and the non-volatile aldehyde, thereby forming the resin.

In a second aspect of the present invention, there is provided a method of forming a resin from an aldehyde oil comprising a volatile aldehyde and a non-volatile aldehyde, comprising the steps of:

(1) separating the volatile aldehyde from the non-volatile aldehyde;

(2) reacting the volatile aldehyde with a cross-linking agent to form an aldehyde-cross-linking agent condensate;

(3) combining the aldehyde-cross-linking agent condensate and the volatile aldehyde component, thereby forming the resin.

A key feature of the invention is the presence of an aldehyde-cross-linking agent condensate (also referred to herein as a "precondensate") formed by reacting a volatile aldehyde with a cross-linking agent. The volatile aldehyde is typically covalently bonded with the cross-linking agent to form the precondensate. The precondensate itself may have cross-linking activity although this is usually and advantageously a modified activity compared to the cross-linking activity of the cross-linking agent used to form the precondensate. The precondensate may have slower or faster cross-linking activity compared to the cross-linking agent, whichever is more controllable and/or suitable for the formation of a desired resin. For example, a precondensate formed using tannin such as mixed tannins (generally, but not always, a slower cross-linking agent than resorcinol) may have higher cross-linking activity than the tannin per se, whereas a precondensate formed using phloroglucinol (generally a faster cross-linking agent than tannin or resorcinol) may have lower cross-linking activity than the phloroglucinol per se.

The methods of the invention thus allow the use of previously unsuitable cross-linking agents for resin formation via use of the precondensate of the invention. The precondensate may furthermore be more stable than unreacted volatile aldehyde and/or cross-linking agent, as some polymerisation has taken place, allowing improved storage and handling of the precondensate for formation of a resin. Additionally, as the precondensate is formed from the volatile aldehyde of an aldehyde oil, more of the aldehyde oil is utilised in the end product resin for example compared to systems where only non-volatile aldehyde was used or where a significant ratio of non-volatile aldehyde to a non-aldehyde cross-linking agent was required to form a resin. The formation of a precondensate also means that less volatile organic compounds (VOCs) to which volatile aldehydes contribute may be emitted in step (3) of the method when the resin is formed, making this step more desirable to the user and safer. As used herein, the term "VOCs" may be defined as organic compounds with a boiling point below 250° C. at a standard atmospheric pressure of 101.3 kPa.

The non-volatile component (for example, any one or more or all of the group consisting of: aldehyde cross-linking agent condensate, cross-linking agent, resin, and solid composite material) in all aspects of the invention may comprise about 0.5-90% residual VOCs (such as residual VOCs from the volatile aldehyde), for example about 1-20% VOCs, about 1-10% VOCs, about 1-5% VOCs, about 10% VOCs, about 5% VOCs, about 1% VOCs or about 0.5% VOCs. In particular, the non-volatile component may comprise less than 10%, less than 5%, or less than 1% VOCs.

It is not necessary that all of the VOCs in the non-volatile component are removed during or following its formation. This is because, in practice, it may be that the most volatile VOCs (say, the initial 10% to 15% of VOCs) are most odorous and/or harmful. Removal of further VOCs beyond an initial 10% to 15% may be advantageous in improving the properties of the non-volatile component. However, an amount of VOCs in the non-volatile component may be useful, for example to improve solubility and/or viscosity.

The reaction of the volatile aldehyde with a cross-linking agent, particularly tannins, during formation of the aldehyde-cross-linking agent condensate of the invention may reduce or eliminate harmful and/or noxious odours associated with the volatile aldehyde. Also, with such odours reduced or eliminated, residual and more pleasant and/or positive odours (such as wood and/or leather odours, particularly from tannins) may be more prevalent and/or accentuated in the aldehyde-cross-linking agent condensate (and/or cross-linking agent, resin, or solid composite material) formed therefrom.

The precondensate and non-volatile aldehyde can be combined in different stoichiometries to influence the characteristics (such as rigidity versus flexibility) of the formed resin. A further advantage of the invention is that resins formed accorded to the methods have a broad range of applications.

The term "resin" as used herein refers to a cross-linked polymer resulting from the combination of a non-volatile aldehyde with an aldehyde-cross-linking agent condensate, optionally in the presence of an additional cross-linking agent and/or polymerisation catalyst (see below). Other cross-linking components, for example resulting from the formation of the aldehyde oil, may also be present in the resin. The term resin as used herein encompasses cured resins and prepolymers (uncured resins), primers, fillers (such as matrix fillers for composites), plastic matrices, adhesives, putties and gels.

According to the invention, the resin may be a bioresin and/or a thermosetting resin. The term "bioresin" refers to a resin whose constituents are derived in total or in part from biological material, particularly renewable sources. Although aldehydes derived from vegetable oils have been used previously in resin formation, the most widely used cross-linking agents were derived from non-biological materials, and the bioresins produced were typically less than 100% or even 80% biological (for example, comprising around 75% biological material). The aldehyde-cross-linking agent condensate (precondensate) of the present invention allows, but is not limited to, biological, renewable material to be used as a cross-linking agent (in the form of the precondensate) and thus formation of pure or a substantially pure bioresin (containing for example more than 95% biological material). Bioresins made according to the present invention can replace existing petrochemical derivatives whilst meeting the emerging legislative and consumer demand for safer products based on sustainable technology.

The aldehyde oil may be derived from a vegetable or animal oil, for example by reductive ozonolysis or by hydroformylation. For example, the aldehyde oil may be derived from a plant oil including any one or more of the group consisting of an algal oil, an unsaturated plant oil such as tung oil, a mono-, di-, and tri-glyceride oil such as rapeseed oil, linseed oil, soya oil, olive oil, castor oil, mustard oil, ground nut (e.g. peanut) oil, and a phenolic oil such as cashew nut shell liquid (CNSL). The aldehyde oil may also be derived from wood oil, sunflower oil, cottonseed oil, palm oil and corn oil.

Oxidation of the plant oil to form an aldehyde oil may be effected by ozonolysis, although other oxidative methods suitable for cleaving unsaturated linkages present in the oils to form aldehyde oils may also be used. Reference is made to the methods for effecting oxidation of plant and animal oils for the formation of suitable aldehyde oils disclosed in WO00/78699 and WO03/050081. Formation of aldehyde oils from vegetable oils or other fatty acid oils using hydroformylation has been described in Guo et al. (2002, supra), Kandanarachchi et al. (2002, supra) and WO2008/073729. In one aspect, an aldehyde oil obtained by hydroformylation is used in a method for the formation of a resin, for example by addition of a cross-linking agent (with or without a precondensate). The resin obtainable from this method is also envisaged.

The volatile aldehyde may comprise a $C_1$-$C_{18}$ aldehyde (such as a $C_1$-$C_{18}$ mono-aldehyde), for example nonanal, hexanal and/or propanal. The volatile aldehyde may additionally or alternatively be defined as an aldehyde removable from a fatty acid oil (such as a vegetable oil or an animal oil) by a separation process, for example vacuum distillation.

The non-volatile aldehyde may comprise a glyceride-bound aldehyde. The non-volatile aldehyde may additionally or alternatively be defined as an aldehyde which is not removable from a fatty acid oil (such as a vegetable oil or an animal oil) by a separation process, for example vacuum distillation. For example, the glyceride-bound aldehyde may be $C_{30}H_{50}O_9$ (obtainable for example following reductive ozonolysis of triolein) and/or higher C forms of glyceride-bound aldehyde.

The cross-linking agent is typically a nucleophile and may be selected for example from any one or more of the group consisting of tannin (such as pine, spruce or quebracho tannin), urea, resorcinol, lignin and phloroglucinol. The cross-linking agent may also be an aromatic, phenol and homologues thereof, polyphenols, glycols and polyols such as ethylene glycol, glycerol and carbohydrates (e.g. sugars and sugar alcohols), amines, amides, thiourea, dicyandiamide, melamine, isocyanates such as MDI, heterocyclic compounds such as furfural, furfuryl alcohol, pyridine and phosphines. The cross-linking agent may be a "natural" or "biological" cross-linking agent. It is also envisaged that the cross-linking agent may be the aldehyde-cross-linking agent of the invention, which (as discussed elsewhere herein) may itself have cross-linking activity.

To improve solubility and dispersion (also referred to herein as "dissolution") of a cross-linking agent such as phloroglucinol, for example for precondensation with a volatile aldehyde from bioresin aldehyde oil, the cross-linking agent may be formulated with water in combination with an organic solvent such as, but not limited to, isopropanol, ethylene glycol, propylene glycol, glycerol, diethylene glycol and/or dipropylene glycol. In addition, an alkali such as sodium hydroxide, potassium hydroxide, sodium carbonate, potassium carbonate, sodium bicarbonate and/or potassium bicarbonate may be employed to further assist dissolution.

More than one cross-linking agent (i.e. a mixture of different cross-linking agents) may be used in the reaction with the volatile aldehyde.

The aldehyde-cross-linking agent condensate may be formed at a temperature of about 0° C.-250° C., such as about 85° C. or about 95° C. Lower temperatures may be suitable where more reactive cross-linking agents are used to form the aldehyde-cross-linking agent condensate.

The aldehyde-cross-linking agent condensate may comprise unreacted (or "excess") cross-linking agent. The methods of forming a resin according to the invention may thus include reacting the volatile aldehyde with an excess of cross-linking agent. In these aspects of the invention, there is a deficiency of the volatile aldehyde compared to the cross-linking agent, so that all the volatile aldehyde is consumed in the formation of the precondensate but full polymerisation is not possible. This means that the aldehyde component in the precondensate is fully reacted. The shelf life of the precondensate is therefore extended, and the precondensate is only able to polymerise fully or further when combined with additional aldehyde, for example the non-volatile aldehyde, such as when the resin is formed. Additional cross-linking agent may be added during the formation of a resin in step 3 of the methods, for example a cross-linking agent selected from any of the cross-linking agents listed above.

Figure 3:
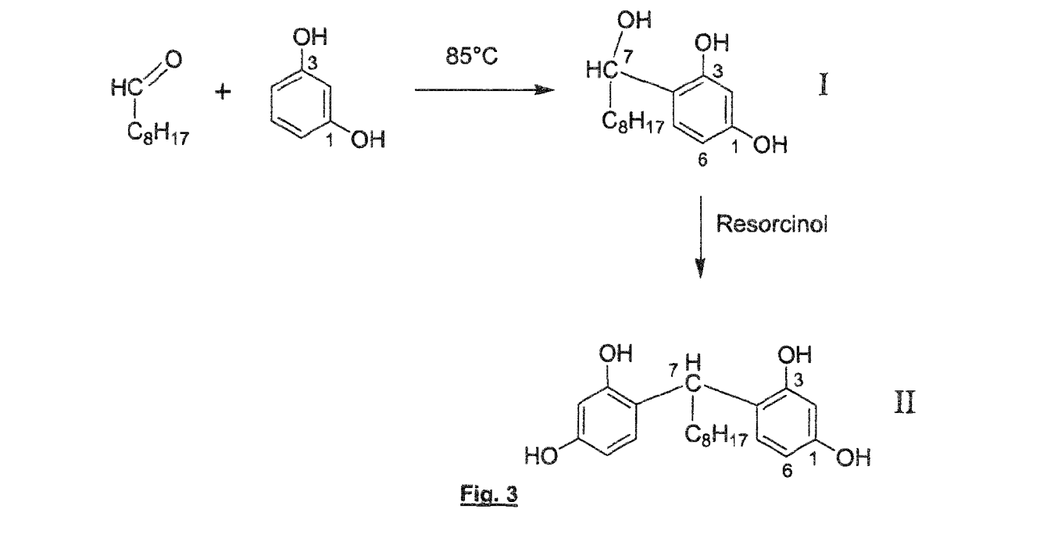
FIG. 3 shows certain of the condensation reaction products formed by reaction of nonanal and resorcinol in the presence of excess resorcinol.

The volatile aldehyde may comprise nonanal, the cross-linking agent comprises resorcinol, and the aldehyde-cross-linking agent condensate may then comprise a linear resorcinol dimer (structure II of FIG. 3) and/or other linear oligomers such as a trimer, tetramer, pentamer, etc., and/or a cyclic resorcinol tetramer linked with nonanal in a 1:1 stoichiometric ratio (i.e. a resorcinarene). Other cyclic oligomers may be present. Structures analogous to structure II of FIG. 3 and the further oligomers described above are also expected to be formed when phloroglucinol replaces resorcinol as the cross-linking agent.

The volatile aldehyde and the non-volatile aldehyde may be derived from the same aldehyde oil. In this aspect of the invention, as noted above, forming the precondensate from the volatile aldehyde prior to forming the resin allows more of the carbon content of the originating aldehyde oil to be incorporated into the final resin, compared with prior art systems such as Pryde et al. (1961, supra).

The aldehyde-cross-linking agent condensate and/or the non-volatile aldehydes for use in the formation of resins according to the present invention may be in the form of oils or solids at ambient temperatures and can subsequently be used either in an undiluted state, or dissolved or dispersed in a suitable solvent or presented as an aqueous emulsion, for example. Addition of an alkali (e.g. NaOH) affords a water soluble or emulsifiable compound (possibly a hydrate of the aldehyde) that can be employed in the aqueous state and optionally cured with the addition of an acid catalyst.

Thus, in a further aspect, the invention provides an aqueous emulsion or an aqueous alkaline solution containing an aldehyde-cross-linking agent condensate and a non-volatile aldehyde (and optionally peroxides and hemiacetals) and/or mixtures thereof. The invention further provides a curable composition comprising this aqueous emulsion and/or aqueous alkaline solution. The invention additionally provides a cured composition of the aforesaid type, for example an acid catalysed cured composition.

Step (3) of the method for forming a resin encompasses in one aspect "curing" of the resin, which may be performed in a variety of different ways. For example, the resin may be capable of undergoing self-crosslinking through a range of chemistries. The properties of the resulting cured resins are influenced by the molecular size of the compounds making up the aldehyde-cross-linking agent condensate and non-volatile aldehyde and the number of reactive sites. Cross-linking mechanisms may include aldehyde polymerisations, polymerisation reactions with residual reducing sugars (e.g. glucose) and/or condensations (e.g. aldol condensations). Curing of the resins may also be effected by the formation of heteropolymers if present in the mixture, for example with compounds such as amines or phenols having free amino or hydroxyl groups, or other nucleophiles. Heteropolymer coupling partners (e.g. co-monomers) may be incorporated either during the preparation of the aldehydes or at the curing stage. Suitable species are generally nucleophiles that can cross-link and become incorporated into the resin structure. Such heteropolymers have modified properties resulting from changes to the cross-linking sites and molecular size of the precursors. Useful properties that can be controlled by the choice of additive include: elasticity, rigidity, brittle fracture, toughness, shrinkage, resistance to abrasion, permeability to liquids and gases, UV resistance and absorbance, biodegradability, density and solvent resistance. The properties of the uncured resins may also be usefully modified using additives to control, for example, the viscosity and flow characteristics of the resin on a filler surface or through spray jets. Examples of materials that can be added to the resins of the invention include aromatics, phenol, resorcinol and other homologues of phenol, CNSL, lignins, tannins and plant and other polyphenols, proteins such as soy protein, gluten, casein, gelatin, and blood albumin; glycols and polyols such as ethylene glycol, glycerol and carbohydrates (e.g. sugars and sugar alcohols); amines, amides, urea, thiourea, dicyandiamide, and melamine; isocyanates such as MDI; heterocyclic compounds such as furfural, furfuryl alcohol, pyridine and phosphines.

Step (3) of the method for forming a resin may be conducted at a temperature about 10° C. to 250° C., for example to produce a cured resin. Curing may proceed over periods of 30 seconds or longer (for example up to many hours). Longer curing times aid moulding and spinning for example. The gel time (i.e. onset of setting during the curing process) can range from 5 seconds to many hours over a temperature range of about 20° C. to 140° C. but at ambient temperature (22° C.) is typically of the order of 30 minutes. The cured resins of the invention may demonstrate excellent water resistance and be impermeable to water at 0-100° C. The heat stability of the cured compositions may be high, for example with degradation temperatures falling within the range 180° C.-250° C. Furthermore, the cured resins and composites made therefrom may have good thermal insulation properties and hence be useful in block or foams form as insulating materials. The cured resins and composites of the invention may have excellent thermal insulation properties. One particular use of the resins of the invention is in the manufacture of timberboard.

The step (3) may be conducted in the presence of a catalyst, for example an alkaline catalyst (such as an alkali metal hydroxide or alkaline earth metal hydroxide, for example sodium hydroxide and potassium hydroxide) or an acid catalyst (such as a sulphonic acid, particularly a substituted sulphonic acid such as an aromatic sulphonic acid, e.g. para-toluenesulphonic acid or methanesulphonic acid). Further examples of catalysts include sulphuric acid and hydrochloric acid, and salts that liberate acids, e.g. ammonium sulphate and ammonium hydrochloride. Further examples of catalysts include Lewis acids such as zinc chloride and zinc acetate, aluminium compounds such as aluminium chloride and boron compounds such as boron trifluoride (e.g. in its trifluoroboroetherate form). Still further examples of catalysts include radical initiators such as dibenzoylperoxide or AIBN.

In another aspect of the invention, there is provided a method for modifying the cross-linking reactivity of a cross-linking agent for resin formation, comprising the step of reacting the cross-linking agent with a volatile aldehyde (for example, from an aldehyde oil) to form an aldehyde-cross-linking agent condensate which has modified cross-linking reactivity compared with unreacted cross-linking agent. The features of this method may be as described for other aspects of the invention. As noted above, modification of the cross-linking agent encompasses increasing or decreasing cross-linking activity, as desired.

Also provided is a cross-linking agent comprising an aldehyde-cross-linking agent condensate obtained by reacting a volatile aldehyde (for example, from an aldehyde oil) with a cross-linking agent. The aldehyde-cross-linking agent condensate may be as defined here for other aspects of the invention. The aldehyde-cross-linking agent condensate (i.e. the volatile aldehyde and/or cross-linking agent components thereof) may be derived from a vegetable oil. Advantages of the aldehyde-cross-linking agent condensate (the "precondensate") are discussed above.

In a further aspect of the invention there is provided a kit for forming a resin, comprising:
(1) an aldehyde-cross-linking agent condensate obtained by reacting a volatile aldehyde with a cross-linking agent; and
(2) a triglyceride-bound aldehyde.

The features of the kit may be as described for other aspect of the invention.

The kit may be in the form of a two-pack system wherein a first pack comprises the aldehyde-cross-linking agent condensate and a second pack comprises the triglyceride-bound aldehyde.

The kit may further comprise an additional cross-linking agent, for example as a component of a or the first and/or a or the second pack and/or in a third pack.

The invention encompasses a two part resin system, comprising a first part including an aldehyde-cross-linking agent condensate obtained by reacting a volatile aldehyde with a cross-linking agent, and a second part including a triglyceride-bound aldehyde. As for the kit of the invention, an additional cross-linking agent may be present, for example as a component of the first and/or second part and/or in a third part. Features of the system may be as described for other aspects of the invention.

The invention provides an improvement over known kits and two part systems for the formation of a resin because the precondensate in particular may be more stable than unreacted volatile aldehyde and/or cross-linking agent used separately in the prior art. Components of the kit may be designed to produce a resin with particular properties, for example by increasing or decreasing the cross-linking reactivity of precondensate and/or additional cross-linking agent and/or by modifying the chemical constituents to allow greater control over the resin formation reaction when the packs or parts are combined. Furthermore, as noted above, the precondensate has reduced VOCs so the kit and system is safer than known equivalents.

The invention also encompasses a resin obtainable by the methods described herein. Resins such as bioresins of the invention have a large number of applications, and examples of uses of the resins include the formation and manufacture of moulded panels, non-woven materials, fibre-glass and other fibre and glass reinforced products, boards, paper treatments, fabric treatments, spun textiles, toys (e.g. children's toys), lubricants, adhesives, castings, automotive components (such as bumpers, fenders, steering wheels, interior panels and mouldings, exterior trim and mouldings), upholstery (as padding or mouldings), binding recycled materials, foundry castings and casting materials (for example binders for refractory articles), bearings, films and coatings, packaging, foams, paint components, pipes, architectural and building products such as door and window frames, varnishes, release controlling coatings such as release controlling coatings for pharmaceuticals, solid prosthetic devices and medical devices, and wood treatment agents, e.g. for preserving and modifying the properties of wood. Articles of the type listed above, formed from resins of the invention, present a further aspect of the invention.

A solid composite material comprising the resin as defined above is envisaged. The resin here may be in the form of a cured thermosetting resin. The solid composite material may further comprise a particulate or fibrous material.

The particulate or fibrous material may be an organic material, for example a lignocellulosic material such as a material selected from wood, straw, hemp, jute, flax, coconut fibre, rice straw and maize. A particularly suitable lignocellulosic material comprises wood particles or wood fibre. Although particulate or fibrous materials from natural sources are suitable, it is also possible to use fibres or particulate materials of man-made type. For example, such fibres or particles can be formed from polymer compositions, examples being recycled plastics. The particulate or fibrous material may alternatively (or additionally) be an inorganic material, for example an inorganic material selected from charcoal, marble (e.g. crushed marble), mineral fibre, mineral particles, ceramics, crushed rock, clay, coal, slate and glass, e.g. fibre glass.

The solid composite material can take various forms such as, for example, sheet form or moulded form. Examples of composite materials in sheet form are boards and panels, particular examples being wood fibre boards such as chipboard, medium density fibre board (MDF), multilayer boards such as plywood, and building boards and panels. The measured properties of test wood particle boards in which the binder used has been derived from an aldehyde of the present invention may meet or exceed those required for boards to be of a standard acceptable in the marketplace and meet or exceed the European Standards for Internal Bond Strength, Thickness Swell, and Bending Strength (Standards EN 319, EN 317, and EN 310, respectively).

In another aspect, the invention provides a solid foam material comprising a matrix formed from a resin of the present invention. The foam material typically is formed by reacting the oxidative cleavage product with an isocyanate, for example methylene diphenyl diisocyanate (MDI). Foams formed in accordance with the invention can be used as inter alia insulating materials, upholstery padding and packaging.

The term "cross-linking agent" as used here refers to a compound which is a nucleophile and which is capable of reacting with an aldehyde (for example, either or both of the volatile aldehyde or the non-volatile aldehyde of the invention) and/or other resin-forming compounds to form a polymer product. The polymer product may, for example, be the aldehyde-cross-linking agent condensate or the resin of the invention. Different cross-linking agents may be combined to form the aldehyde-cross-linking agent condensate and/or the polymer product.

The invention will now be described in further detail and with reference to particular non-limiting examples and the following drawings, in which.

EXAMPLES

A known bioresin-producing system using aldehyde oil derived from a vegetable oil combined with resorcinol as a cross-linking agent and alkali catalysis provides satisfactory performance in many applications but has some disadvantages as noted above. Improvements relating to the present invention are elaborated below.

A system which employs a natural cross-linking agent of non-petrochemical origin (such as tannin) instead of resorcinol is one desirable aspect of the present invention and is investigated in certain of the experiments below. A number of bioresin formulations using tannin as cross-linking agent were prepared, using a reduced VOCs or low odour approach of forming an aldehyde-cross-linking agent condensate (also referred to herein as a "precondensate") from volatile aldehydes of an aldehyde oil, and to study the associated physical performance of the formulations. Bioresins according to the invention formed using resorcinol as cross-linking agent are also exemplified and characterised.

Example 1

Preparation of Tannin Incubations and VOCs Assessment

Aldehyde oil obtained from commodity rape seed oil using the optimised reductive ozonolysis process described in WO03/0500081 was fractionated by rotary evaporation to separate the volatile aldehyde components from the non-volatile aldehydes. The volatile fraction (VF°, or volatile aldehyde fraction; principally nonanal) was then recombined variously with tannin extracted from mimosa bark and incubated at 85° C. or 95° C. over a period of up to 67 hours, and the reduction in volatile aldehydes determined by measurement of nonanal using gas chromatography-mass spectrometry (GC-MS).

In detail, a 1 g sample of the precondensate incubation was prepared as a 10% w/w solution in methanol/water (1:1). The sample was spiked with 50 µl n-octanal internal standard, then 0.5 µl samples (split 100:1) were analysed by GC-MS using a Hewlett Packard 5890 II gas chromatograph linked to a VG-TRIO 1 mass spectrometer. The GC column used was a 60 m×0.32 mm I.D. 5.0 µm df DB1 capillary column, programmed from 35° C. (1 min.) to 250° C. (14.4 min.) at 25° C./min. Electron ionisation mass spectrometry was performed by scanning m/z 25 to m/z 250. The data are shown below in Table 1.

TABLE 1

Nonanal decay with time for a variety of tannin incubations at 85° C. or 95° C.

| Incubation Time (hours) | 1 Nonanal Remaining % (85° C.) | 2 Nonanal Remaining % (95° C.) | 3 Nonanal Remaining % (85° C.) | 4 Nonanal Remaining % (85° C.) | 5 Nonanal Remaining % (85° C.) |
|---|---|---|---|---|---|
| 0.0 | 100.0 | 100.0 | 100.0 | 100.0 | 100.0 |
| 1.5 | — | 82.5 | — | — | — |
| 2.0 | 86.5 | — | — | — | — |
| 3.5 | — | 67.5 | — | — | — |
| 4.0 | 74.0 | — | — | — | — |
| 16.0 | — | — | — | — | 29.0 |
| 20.0 | — | — | — | — | 12.2 |
| 21.5 | — | 17.9 | — | — | — |
| 22.0 | — | — | 63.2 | 36.7 | — |
| 24.5 | 24.0 | — | — | — | — |
| 28.0 | — | 6.3 | — | — | — |
| 43.0 | — | — | 37.7 | 11.3 | — |
| 45.0 | 4.4 | 1.1 | — | — | — |
| 67.0 | — | — | — | 2.7 | — |

The compositional detail for samples 1 to 5 in Table 1 is:
1. 1 g VF+17.85 g 56% tannin solution (85° C.)
2. 1 g VF+17.85 g 56% tannin solution (95° C.)
3. 1 g VF+26.8 g 56% tannin solution (85° C.)
4. 2 g VF+2 g AOG+35.7 g 56% tannin solution (85° C.)
5. 10 g AO+35.7 g 56% tannin solution (85° C.).

Control "ranging" experiments showed that using the equivalent of 1 part bioresin aldehyde oil to 2 parts tannin is an effective starting quantity to use, so this ratio was adopted as "standard" for the purposes of the examples. For the incubations shown in Table 1, the total tannin quantity was incubated with the volatile fraction (VF), with or without the non-volatile glyceride-bound aldehyde (AOG) fraction, or with unfractionated aldehyde oil (AO), as indicated above. For subsequent performance assessment, the tannin-VF incubations were blended variously with the glyceride-bound aldehyde (AOG) fraction, as described below.

As can be seen from Table 1, when unfractionated aldehyde oil (AO) is incubated with tannin (control experiment) there is a decline in VOCs (as indicated by nonanal decline) but much more slowly than with the volatile fraction (VF) alone, as the tannin is able to react with both glyceride-bound aldehyde as well as the volatile aldehydes. The inclusion of a small quantity (20% stoichiometric amount) of the non-volatile AOG fraction also slows down the VOCs reaction but the curve is quite similar to the incubations with the VOCs fraction only. Therefore, it is feasible according to the invention to include non-volatile aldehyde in the formation of the aldehyde-cross-linking agent condensate, if desired.

The incubation at 95° C. showed a more rapid decline in VOCs than for the equivalent at 85° C. so, from a processing point of view, increasing the reaction temperature during production of the aldehyde-cross-linking agent condensate can be advantageous to save time. However, in the present study the end product showed no performance differences with an incubation temperature at 85° C. or 95° C. when allowed to proceed to >95% VOCs reduction, so for practical reasons 85° C. was adopted.

Increasing the amount of tannin to 1.5× the standard amount brought the VOCs decay curve at 85° C. to be equivalent to the 95° C. curve with the standard tannin. This arises since there is an even greater excess of nucleophile so a faster reaction with aldehydes. Adoption of the greater nucleophile quantity would be considered suitable in most (but not all) circumstances if this leads to an improved performance of the material upon combining or recombining with the non-volatile fraction (AOG), and this was not found to be the case in the present study. Hence, for the purposes of a more extensive evaluation of catalysis, conditions adopted were the incubation of the volatile fraction only at 85° C. for 46 hours with a tannin quantity consistent with a 2:1 ratio wrt aldehyde oil. This ensured a precondensed formulation in which >95% VOCs had been consumed.

We considered that the same or a higher degree of VOCs reduction would be achieved at much shorter incubation times by the careful use of catalysts during incubation, and investigated this in Example 2 below.

Example 2

Preparation of Further Tannin Incubations; Effect of Tannin Catalyst and/or Temperature In one experiment, 5 g of a 50% w/w aqueous solution of different types of tannin as indicated below was incubated with 0.28 g of the volatile fraction removed from a rapeseed oil-derived bioresin aldehyde oil, the principal constituent of which was nonanal. Sodium hydroxide catalyst was added as indicated below. The percentage of nonanal remaining in the incubations was determined by the periodic removal of sub samples and quantitative analysis by GC-MS using octanal as a spiked internal standard.

Figure 4:
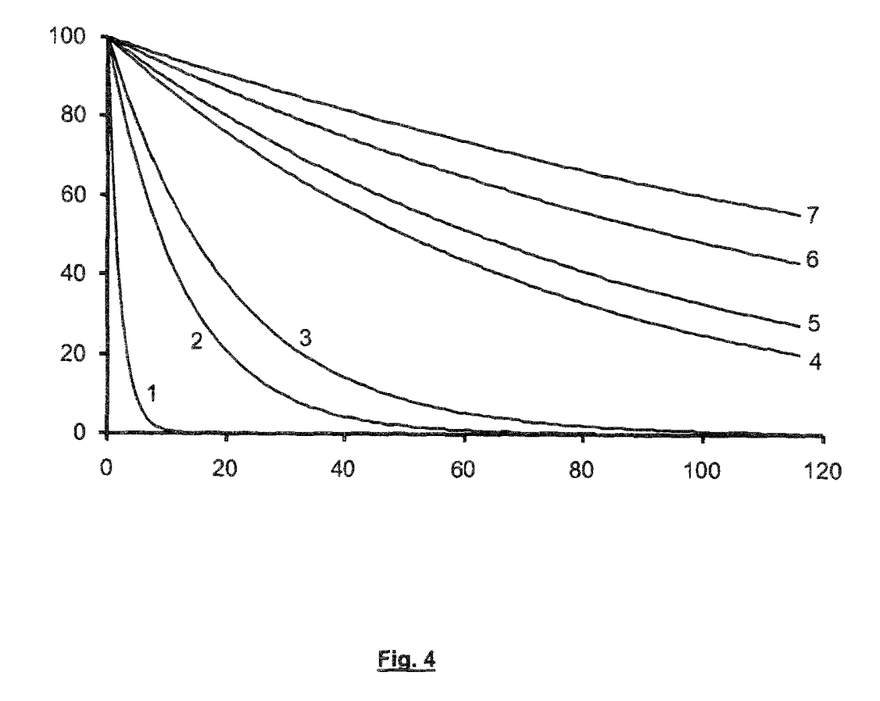
FIG. 4 is a graph showing reduction of nonanal (an indicator of VOCs) during formation of various aldehyde-cross-linking agent condensates. The x-axis represents incubation time at 85° C. (in hours) and the y-axis the percentage of nonanal remaining. The numbered lines are explained in Example 2 below.

The numbered lines in FIG. 4 represent (1) quebracho tannin with 3% w/w sodium hydroxide catalyst; (2) spruce tannin with 2% w/w sodium hydroxide catalyst; (3) spruce tannin with no added catalyst (4) Chestnut tannin with 3% w/w sodium hydroxide catalyst; (5) quebracho tannin with 1% w/w sodium hydroxide catalyst; (6) quebracho tannin with no added catalyst; and (7) chestnut tannin with 1% w/w sodium hydroxide catalyst.

The results shown in FIG. 4 demonstrate that an aldehyde-cross-linking agent condensate in which effectively all of the VOCs (as determined by nonanal) from the starting volatile aldehyde have been consumed can be achieved using an appropriate catalyst (such as sodium hydroxide) in combination with a suitable cross-linking agent (here, a tannin such as quebracho tannin).

In another experiment, 5 g of a 56% w/w aqueous solution of pine or mimosa tannin was incubated with 0.28 g of the volatile fraction removed from a rapeseed oil-derived bioresin aldehyde oil, the principal constituent of which was nonanal.

Figure 5:
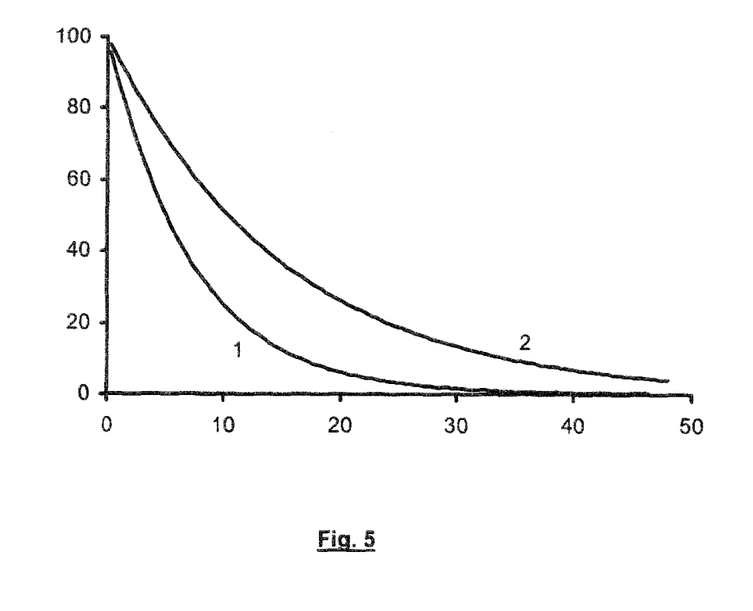
FIG. 5 is a graph showing reduction of nonanal (an indicator of VOCs) during formation of aldehyde-cross-linking agents from pine and mimosa tannins. The x-axis represents incubation time at 85° C. (in hours) and the y-axis the percentage of nonanal remaining. The numbered lines are explained in Example 2 below.

The results are shown in FIG. 5, in which the horizontal axis represents the incubation time at 85° C. (hours) and the vertical axis the percentage of nonanal remaining, as determined by the periodic removal of sub samples and quantitative analysis by GC-MS using octanal as a spiked internal standard. The numbered lines represent: (1) pine tannin with no added catalyst; (2) mimosa tannin with no added catalyst.

These results from FIG. 5 demonstrate that effectively all of the VOCs (as determined by nonanal) from the starting volatile aldehyde can be eliminated during production of an aldehyde-cross-linking agent condensate if an appropriate cross-linking agent (for example, pine tannin) is used, even in the absence of a catalyst.

Example 3

Characteristics of a Tannin Bioresin Formed from Precondensate

A bioresin formed inter alia from the precondensate and tannin was prepared as described in Example 1 and selected to have minimal VOCs as determined by GC analysis. The bioresin was prepared using a two-pack system comprising the following components: (1) a aldehyde-cross-linking agent condensate in the form of a tannin/nonanal precondensate (TN), 58.36% solids in water; and (2) a non-volatile aldehyde in the form of an aldehyde oil glyceride fraction (AOG), 100% solids. The bioresin was prepared from the two components by mixing AOG and TN in the ratio 1:4.46 (AOG:TN) to be equivalent to the overall composition of a control mixture of tannin and aldehyde oil in the ratio 2:1 (tannin:aldehyde oil). As mixed, the bioresin had 65.6% solids.

3.1 Physical Properties

Resin was prepared by mixing the components of the two-pack system and diluting it to 50% resin solids with water. The viscosity of the solution was determined across a range of temperatures and the results are shown in Table 2.

TABLE 2

The effect of temperature on the viscosity of bioresin formed using precondensate

| Temperature (° C.) | Viscosity (cP) |
|---|---|
| 20 | 10,500 |
| 30 | 4,000 |
| 40 | 1,000 |
| 50 | 275 |

The viscosity of the bioresin is highly sensitive to temperature and handling can be improved significantly by heating from ambient to 40-50° C.

3.2 Curing Rate and Binder Strength Using Alkaline Catalyst

The bioresin was tested across a range of binder formulations to determine the rate of curing and the strength of the resulting binder. Formulations were standardised on the mass of resin solids, and controls were included for comparison from standard resorcinol-catalysed bioresin systems and non-precondensed (i.e. unfractionated) aldehyde oil/tannin mixtures.

Binder strength was assessed by preparing sand/resin composite discs. The discs were prepared by mixing sand with resin formulated as a 30% resin solids emulsion in water to provide a loading on the sand of 3% w/w. The breaking force under test was recorded as a measure of the binder strength. Binders were formulated from AOG/TN combined as above together with variable additions of sodium hydroxide catalyst, 1%-7%, and urea, 0%-10% on a resin basis. Earlier work with resorcinol resins had indicated the effect of urea on increasing the curing rate of binders.

Binder formulations were prepared at 30% resin solids as emulsions in water and applied to sand to give a loading of 3% resin on the test disc. Control formulations had equivalent loadings. Test discs, 2.5 cm diameter×0.5 cm thick, were prepared by filling the wet sand/binder mix into steel moulds and heating them for the required time on a hotplate set to the required curing temperature. Discs were allowed to cool and subjected to the mechanical test. The results obtained for curing at 150° C. for 10, 20, 30 or 40 minutes, together with the formulation details for urea and alkali are shown in Table 3 and compared with controls.

TABLE 3

The effect of alkali and urea on resin binder strength at 150° C.

| Formulation | Urea (%) | Alkali (%) | Binder Breaking Stress (kg) | | | |
|---|---|---|---|---|---|---|
| | | | 10 min | 20 min | 30 min | 40 min |
| AO/R1 | 0 | 4 | 14 | 22 | 24 | 26 |
| AO/T1 | 0 | 2 | 2 | 4 | 3 | 4 |
| AO/T2 | 6 | 4 | 13 | 18 | 14 | 17 |
| PCR | 0 | 1 | 18 | 26 | 26 | 26 |
| TN/G1 | 0 | 2 | 5 | 7 | 7 | 8 |
| TN/G2 | 6 | 3 | 14 | 17 | 16 | 14 |
| TN/G3 | 0 | 4 | 7 | 12 | 12 | 12 |
| TN/G4 | 2 | 4 | 14 | 20 | 19 | 22 |
| TN/G5 | 4 | 4 | 20 | 23 | 25 | 22 |
| TN/G6 | 6 | 4 | 25 | 23 | 24 | 22 |
| TN/G7 | 10 | 4 | 19 | 19 | 19 | 20 |
| TN/G8 | 0 | 7 | 13 | 14 | 6 | 2 |

The different resin types depicted in Table 3 are:

| Code | Resin Type |
|---|---|
| AO/R | Aldehyde oil mixed with resorcinol (1:0.3), no precondensation |
| AO/T | Aldehyde oil mixed with tannin (1:2), no precondensation |
| PCR | Aldehyde oil precondensed with resorcinol (1:0.3) |
| TN/G | AOG mixed with TN precondensate (1:4.46). |

The results demonstrate a range of binder quality based on the strength achieved under the chosen curing conditions. The PCR control is the target with high strength achieved in 20 minutes. The benefit of precondensation (i.e. the formation of an aldehyde-cross-linking agent condensate) is shown by comparing PCR with AO/R1. The non-precondensed mixture achieves a similar strength to PCR but requires a longer curing time. The results for AO/T1 indicate the relatively poor performance for tannin binder without precondensation. Even increased catalyst and urea addition are not able to improve that performance sufficiently, as shown by AO/T2.

The tannin precondensate bioresins show significant improvement over the straight mixtures AO/T resins. Whilst low catalyst and no urea resins were very slow to cure, TN/G1 with increased catalyst and urea addition was very effective in increasing the curing rate and eventual binder strength. Very high catalyst at 7% or excessive urea addition, i.e. 10%, was shown to be detrimental to binder quality. Optimal additions were found to be in the range 4-6% urea at 4% catalyst and these formulations can achieve >90% of the value observed for PCR in 30 minutes at 150° C.

Selected formulations were tested at 170° C. and results are shown in Table 4.

TABLE 4

The effect of addition level of alkali and urea on binder strength at 170° C.

| Formulation | Urea (%) | Alkali (%) | Binder Breaking Stress (kg) | | | |
|---|---|---|---|---|---|---|
| | | | 10 min | 20 min | 30 min | 40 min |
| PCR | 0 | 1 | 25 | 26 | 26 | 26 |
| TN/G9 | 6 | 2 | 14 | 15 | 17 | 19 |
| TN/G2 | 6 | 3 | 23 | 23 | 22 | 21 |
| TN/G6 | 6 | 4 | 23 | 21 | 25 | 26 |

The different resin types depicted in Table 4 were as described for Table 3.

At this higher temperature, the performance of TN/G2 is much improved but once again the optimum performance is seen with TN/G6. The low catalyst addition of TN/G9 results in a slow curing rate.

2.4 Curing Rate and Binder Strength Using Acid Catalyst

It has been recognised from other work that curing of the tannin resins is effectively catalysed by the addition of strong organic acids such as toluene sulphonic or methane sulphonic acids. Whilst less desirable for many applications than the addition of low levels of alkali, the acid route is generally more effective for simple tannin/aldehyde oil mixtures. The effect of methanesulphonic acid on the precondensed tannin system was investigated here, and the results shown in Table 5. Increasing the curing temperature over the range 130° C. to 220° C. at 13% acid (on a resin basis) increased the rate of curing significantly and at 220° C. the tannin precondensed system was equivalent to a control, alkali catalysed, resorcinol PCR resin. At lower temperatures, the acid cured system was inferior to the alkali binders discussed above even though much higher addition levels were used for the acid system. Reducing the acid addition to 7% resulted in a further decrease in performance. Addition of urea was ineffective at increasing the strength of the binder at 150° C. as was further addition of acid up to 20% where there was evidence of hydrolysis damage to the cured resin after 40 minutes heating. The poor performance of the urea-supplemented binder was unexpected given the positive effect of urea under alkaline curing conditions.

TABLE 5

Strength of acid cured binder formulations at 130° C. to 220° C.

| Temperature (° C.) | Urea (%) | Acid (%) | Binder Breaking Stress (kg) | | | |
|---|---|---|---|---|---|---|
| | | | 10 min | 20 min | 30 min | 40 min |
| 130 | 0 | 13 | 15 | 15 | 15 | 17 |
| 150 | 0 | 7 | 9 | 11 | 9 | 13 |
| 150 | 0 | 13 | 18 | 18 | 19 | 20 |
| 150 | 4 | 13 | 5 | 4 | 2 | 2 |
| 150 | 0 | 20 | 17 | 17 | 19 | 5 |
| 170 | 0 | 13 | 20 | 19 | 19 | 23 |
| 190 | 0 | 13 | 18 | 20 | 23 | 25 |
| 220 | 0 | 13 | 26 | 26 | 25 | 26 |
| PCR 220 Control | 0 | 0 | 26 | 26 | 26 | 26 |

Example 4

Analysis of Gel Times and VOC Depletion for Various Resins

In one experiment, 4 samples of various pre-condensed tannins as indicated in Table 6 below were prepared by incubating 50% w/w aqueous tannin solutions (20 parts) with the volatile fraction from bioresin aldehyde oil (1 part) at 85° C. The various pre-condensed tannins were then subjected to gel time tests at 85° C. and compared to the native, non-pre-condensed tannins by combination with the non-volatile glyceride-bound aldehyde from rapeseed oil-derived bioresin.

TABLE 6

Gelling time of tannin precondensates and native tannin

| Tannin | Gel Time (min) of Precondensed tannin | Gel Time (min) of Native tannin |
| --- | --- | --- |
| Chestnut CH3 | 4.0 | 6.0 |
| Quebracho QB2 | 2.0 | 4.0 |
| Spruce SP1 | 4.0 | 4.0 |
| Mimosa | 3.0 | 5.5 |

The results in Table 6 demonstrate that pre-condensation led to the shortening of gel times by 30-50% except in the case of spruce tannin where no difference was observed at the gelling temperature used.

In another experiment, the gel time test was modified to accommodate the very high reactivity of the phloroglucinol precondensate (PGN; i.e. phloroglucinol pre-condensed with the volatile fraction removed from rapeseed oil-derived bioresin aldehyde oil) with AOG (i.e. the non-volatile glyceride residue following the removal of the volatile fraction of the vegetable oil-derived bioresin aldehyde oil).

As shown in Table 7 below, under standard test conditions of 85° C. with 5% sodium hydroxide catalyst, the PGN reacted instantly. Therefore, further testing was carried out (see below) with no catalyst addition and at different temperatures.

TABLE 7

Gelling time of phloroglucinol precondensate (PGN)

| Temperature ° C. | Gel Time (min) No catalyst | Gel Time (min) 5% NaOH catalyst |
| --- | --- | --- |
| 55 | 15 | 0.25 |
| 70 | 7 | 0.25 |
| 85 | 4 | 0.00 |

In a final experiment of this example, 2.22 g of phloroglucinol as an aqueous emulsion in 6.5 g water was incubated with 1.25 g of the volatile fraction removed from a rapeseed oil-derived bioresin aldehyde oil, the principal constituent of which was nonanal.

Figure 6:
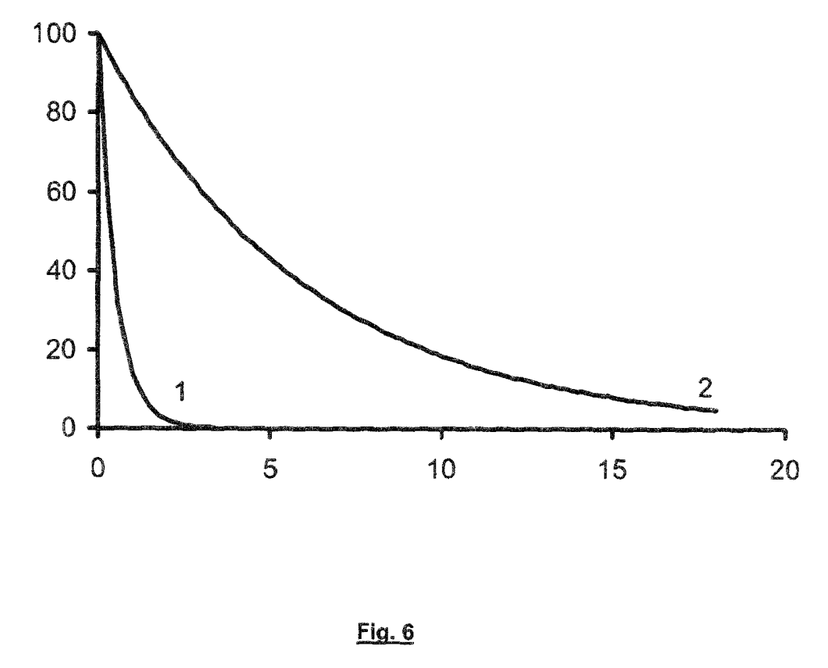
FIG. 6 is a graph showing reduction of nonanal (an indicator of VOCs) during formation of aldehyde-cross-linking agents from phloroglucinol. The x-axis represents incubation time at 85° C. (in hours) and the y-axis the percentage of nonanal remaining. The numbered lines are explained in Example 6 below.

The results are shown in FIG. 6, in which the horizontal axis represents the incubation time (hours) and the vertical axis the percentage of nonanal remaining, as determined by the periodic removal of sub samples and quantitative analysis by GC-MS using octanal as a spiked internal standard. The numbered lines represent: (1) 85° C. incubation temperature; (2) 45° C. incubation temperature.

FIG. 6 demonstrates that a faster reduction of VOCs can be achieved during formation of an aldehyde-cross-linking agent condensate using a higher incubation temperature, and that certain precondensates such as PCN do not require catalyst for their formation.

Example 7

Characteristics of Products Made from PGN-Derived and Other Resins

In one experiment, the Modulus of Rigidity (GPa) was measured for chopped glass mat composite panels made with resin formulations prepared using phloroglucinol precondensate (PGN, as described above), the principal constituent of which was nonanal, and AOG (as described above).

For the samples shown in Table 8 below, a 3 ply, 9 cm×3 cm composite panel was prepared using chopped glass mat (c. 300 g/m$^2$). The binder was prepared by mixing PGN with AOG and adding catalyst as 30% sodium hydroxide to give the required catalyst level. Binder was applied to the mat and subsequent layers built up. The composite was cured at 80° C. for 2 hours upwards. The panels, together with a control using resorcinol as a cross-linking agent, were compared for Modulus of Rigidity (GPa). In order to improve the overall dispersibility of the binder, a formulation was prepared also containing 30% isopropanol.

TABLE 8

Strength characteristics of products formed using PGN precondensate

| Cross-linking agent | Catalyst (%) | IPA solvent (Y/N) | GPa |
| --- | --- | --- | --- |
| PGN | 0 | N | 0.8 |
| PGN | 1 | N | 1.2 |
| PGN | 2 | N | 1.1 |
| PGN | 2 | Y | 1.6 |
| Resorcinol | 4 | N | 1.5 |

As noted previously, to improve solubility and dispersion of phloroglucinol, such as for pre-condensation with the volatile fraction from bioresin aldehyde oil, it can be formulated with water in combination with organic solvents such as, but not limited to, isopropanol, ethylene glycol, propylene glycol, glycerol, diethylene glycol, dipropylene glycol. In addition, alkalis such as sodium hydroxide, potassium hydroxide, sodium carbonate, potassium carbonate, sodium bicarbonate, potassium bicarbonate and so on, can be employed to further assist dissolution. In the example above, the improved solution/dispersibility afforded by the use of isopropyl alcohol solvent was sufficient to elevate the performance of the composite panel to that of the resorcinol control.

In a further experiment, mechanical data was for composite panels (3 ply, 9 cm×3 cm×2 mm) made from chopped glass mat (c. 300 g/m$^2$) and resin formulations made variously from AOG, P (phloroglucinol) and TN (mimosa tannin precondensed with the volatile fraction from aldehyde oil).

Table 9 below shows panels made with resins based on mimosa tannin cross-linking agent alone, phloroglucinol cross-linking agent alone, and with combinations of both. The % BOR is the percentage addition based on total resin solids. Under these test conditions, chosen to be discriminatory, the TN performance could be enhanced considerably by a relatively modest addition of PG (PT1) to give a performance comparable to and possibly exceeding that of PG alone:

TABLE 9

Mechanical data for composite panels

| Code | Resin Cross-linking agent(s) | TN (% BOR) | P (% BOR) | Resin AOG (% BOR) | Yield Stress (MPa) | Yield Strain (%) | Flexural Modulus (GPa) |
|---|---|---|---|---|---|---|---|
| T1 | TN | 62 | 0 | 38 | 15 | 4.2 | 0.4 |
| T2 | TN | 73 | 0 | 27 | 13 | 3.1 | 0.4 |
| T3 | TN | 73 | 0 | 27 | 12 | 1.5 | 0.8 |
| P1 | P | 0 | 27 | 73 | 62 | 2.6 | 2.4 |
| PT1 | P/TN | 38 | 12 | 50 | 83 | 3.2 | 2.6 |
| PT2 | P/TN | 50 | 7 | 43 | 37 | 3.8 | 1.0 |

Example 8

Structure of Nonanal-Resorcinol Precondensate

The incubation of nonanal (the principal constituent of the volatile aldehyde fraction removed from aldehyde oil) and resorcinol was performed at a 1:2 stoichiometric ratio (nonanal:resorcinol) at 85° C. in a solvent-free system. The nonanal was consumed in less than 5 hours yet, as shown in Table 6, the resorcinol continues to be consumed until it steadies after around 24 hours with around 40% remaining unreacted. This demonstrates how new structures are formed after the initial uptake of nonanal. It is evident that initially, nonanal will be bound to a single resorcinol molecule (see structure I in FIG. 3) to form an intermediate alkylol derivative, before quickly reacting with a second resorcinol molecule to form a dimer (structure II in FIG. 3). However, if only the dimer were formed then all resorcinol would be expected to be consumed but since its consumption plateaus at around 22 hours, this shows that further structures such as the cyclic tetramer (i.e. resorcinarene, a cyclic resorcinol tetramer linked with nonanal), where the stoichiometric ratio of nonanal:resorcinol consumed is 1:1, is formed in significant quantity in the presence of excess resorcinol. The consumption of >50% resorcinol suggests that some of the dimer also remains. The fact that resorcinol reaches a point where little more is consumed suggests that the end product is limited to an oligomer which does not polymerise further in the absence of free aldehyde, rather than a linear polymer. However, the nonanal-resorcinol precondensate would also comprise structures such as larger linear oligomers, for example trimers, tetramers, pentamers, etc. (not shown in FIG. 3).

TABLE 10

Resorcinol depletion during formation of a nonanal-resorcinol condensate starting with 2:1 molar excess over nonanal

| Time (hours) at 85° C. | Resorcinol Remaining (%) |
|---|---|
| 0 | 100 |
| 8 | 60 |
| 12 | 51 |
| 22 | 41 |
| 54 | 38 |

Example 9

Use of a Mixture of Cross-Linking Agents in Resin Formation

In this example, mimosa tannin, 200 g of a 50% solution in water, is mixed with 10 g of its volatile fraction. Catalyst is added as 7 g of 30% sodium hydroxide solution and the mixture is incubated at 85° C. for 25 hours. Phloroglucinol, 30 g, and its volatile fraction, 17 g, is added to the mixture which is incubated for a further 5 hours at 85 C. The mixture is cooled to ambient temperature and formulated with 110 g of non-volatile glyceride-bound aldehyde (AOG) fraction to make a thermosetting resin.

Here, the resin is prepared by first precondensing the volatile fraction with a mixture of tannin and phloroglucinol at the same time rather than preparing two separate cross-linking agents (TN and P) for formulation with AOG. This approach is beneficial as only one cross-linking agent needs to be prepared and blended with AOG rather than two (as shown for example for "PT1" in Example 7 above).

Example 10

Use of Resorcinol Precondensate for Resin Formation

Aldehyde oil was fractionated into volatile and non-volatile components by rotary evaporation. The volatile component (1 part) was precondensed with resorcinol (1.75 parts) by incubation at 85 deg C. for 22 hours, and the resulting precondensate combined with the non-volatile fraction in the ratio 8.0 (non-volatile) to 5.5 (precondensate) to form a bioresin. The bioresin was formulated into a binder emulsion with water to 30% solids and added to sand at 10% giving a loading of 3% w/w on the basis of sand. Catalyst was included as sodium hydroxide at 1% w/w on the basis of resin solids. The sand was moulded into discs 2.5 cm diameter×0.5 cm thick. The discs were cured at 200° C. for 10 minutes, cooled and then subjected to a breaking test as described earlier for the tannin precondensates. The breaking force of the bioresin was equivalent to that obtained with a similar loading of a phenol formaldehyde resin.

CONCLUSIONS

It has been demonstrated in certain of the experiments shown here that by selectively incubating a tannin or resorcinol nucleophile as cross-linking agent with a volatile aldehyde in the form of a volatile fraction derived from an aldehyde oil, it is possible to form an aldehyde-cross-linking agent condensate (the "precondensate") with useful properties such as cross-linking activity when combined with non-volatile aldehydes for the formation of a resin. Additionally, increase the performance of a resin in the form of a binder made from the precondensate and the non-volatile aldehydes (the AOG fraction) from the aldehyde oil was similar to that of a standard resorcinol-catalysed bioresin. Furthermore, for the production of bioresins, the use of an alkali such as sodium hydroxide has been shown to be the catalyst of choice when working at curing temperatures below 200° C.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

The invention claimed is:

1. A method of forming a resin from an aldehyde oil comprising a volatile aldehyde and a non-volatile aldehyde, comprising the steps of: (1) separating the volatile aldehyde from the non-volatile aldehyde; (2) reacting the volatile aldehyde with a cross-linking agent to form an aldehyde-cross-linking agent condensate; (3) combining the aldehyde-cross-linking agent condensate and the non-volatile aldehyde, thereby forming the resin.

2. The method according to claim 1, wherein the resin is a bioresin and/or a thermosetting resin.

3. The method according to claim 1, wherein the aldehyde oil is derived from a vegetable or animal oil.

4. The method according to claim 3, wherein the aldehyde oil is derived from a plant oil selected from any one or more of the group consisting of an algal oil, an unsaturated plant oil, a mono-, di-, and tri-glyceride oil, and a phenolic oil.

5. The method according to claim 1, wherein the volatile aldehyde comprises a $C_1$-$C_{18}$ aldehyde.

6. The method according to claim 1, wherein the non-volatile aldehyde comprises a glyceride-bound aldehyde.

7. The method according to claim 1, wherein the cross-linking agent comprises any one or more of the group consisting of tannin, urea, resorcinol, lignin and phloroglucinol.

8. The method according to claim 1, wherein the aldehyde-cross-linking agent condensate is formed at a temperature of about 0° C.-250° C.

9. The method according to claim 1, wherein the aldehyde-cross-linking agent condensate comprises unreacted cross-linking agent resulting from use of an excess of said cross-linking agent relative to said volatile aldehyde to form said aldehyde-cross-linking agent condensate in step (2).

10. The method according to claim 1, wherein step (3) is conducted in the presence of additional cross-linking agent.

11. The method according to claim 1, wherein the volatile aldehyde comprises nonanal, the cross-linking agent comprises resorcinol, and the aldehyde-cross-linking agent condensate comprises a resorcinol dimer and/or one or more other linear oligomers and/or cyclic oligomers.

12. The method according to claim 1, wherein the volatile aldehyde and the non-volatile aldehyde are derived from the same aldehyde oil.

13. The method according to claim 1, wherein step (3) is conducted at temperatures of about 10° C. to 250° C.

14. The method according to claim 1, wherein step (3) is conducted in the presence of a catalyst.

15. A method for modifying the cross-linking reactivity of a cross-linking agent for resin formation, comprising reacting the cross-linking agent with a volatile aldehyde to form an aldehyde-cross-linking agent condensate which has modified cross-linking reactivity compared with unreacted cross-linking agent.

16. The method according to claim 1, wherein the aldehyde oil is derived from a vegetable or animal oil by reductive ozonolysis or hydroformylation.

17. The method according to claim 3, wherein the aldehyde oil is derived from an unsaturated plant oil selected from tung oil and sunflower oil.

18. The method according to claim 3, wherein the aldehyde oil is derived from a mono-, di-, or tri-glyceride oil selected from the group consisting of oil seed rape, linseed, soya, olive oil, castor oil, mustard seed oil, and ground nut oil.

19. The method according to claim 3, wherein the aldehyde oil is derived from a phenolic oil.

20. The method according to claim 19, wherein said phenolic oil is cashew nut shell liquid (CNSL).

21. The method according to claim 5, wherein said $C_1$-$C_{18}$ aldehyde is a $C_1$-$C_{18}$ mono-aldehyde.

22. The method according to claim 21, wherein said $C_1$-$C_{18}$ aldehyde mono-aldehyde is selected from the group consisting of nonanal, hexanal and propanal.

23. The method according to claim 1, wherein the aldehyde-cross-linking agent condensate is formed at a temperature of about 85° C.

24. The method according to claim 1, wherein the aldehyde-cross-linking agent condensate is formed at a temperature of about 95° C.

25. The method according to claim 1, wherein the volatile aldehyde comprises nonanal, the cross-linking agent comprises resorcinol, and the aldehyde-cross-linking agent condensate comprises a resorcinol dimer and/or one or more other linear oligomers selected from a trimer, tetramer, and pentamer.

26. The method according to claim 1, wherein the volatile aldehyde comprises nonanal, the cross-linking agent comprises resorcinol, and the aldehyde-cross-linking agent condensate comprises a resorcinol dimer and/or a resorcinarene cyclic oligomer.

27. The method according to claim 14, wherein said catalyst is an alkaline catalyst.

28. The method according to claim 27, wherein said alkaline catalyst is selected from alkali metal hydroxide and alkaline earth metal hydroxide catalysts.

29. The method according to claim 27, wherein said alkaline catalyst is sodium hydroxide.

30. The method according to claim 14, wherein said catalyst is an acid catalyst.

31. The method of claim 30, wherein said acid catalyst is a sulfonic acid catalyst.

32. The method of claim 31, wherein said sulfonic acid catalyst is an aromatic sulfonic acid.

33. The method of claim 32, wherein said aromatic sulfonic acid is p-toluenesulfonic acid or methanesulfonic acid.

* * * * *